United States Patent [19]

Saxena et al.

[11] Patent Number: 4,693,969

[45] Date of Patent: Sep. 15, 1987

[54] REAGENT FOR USE IN A SANDWICH SOLID-PHASE ENZYME-IMMUNOASSAY AND PROCESS FOR EMPLOYING SAME

[75] Inventors: Brij B. Saxena, Englewood; Premila Rathnam, Englewood Cliffs, both of N.J.

[73] Assignee: Cornell Research Foundation, Inc., Ithaca, N.Y.

[21] Appl. No.: 607,025

[22] Filed: May 4, 1984

[51] Int. Cl.[4] .................. G01N 33/535; G01N 33/545; G01N 33/74; C12N 9/96
[52] U.S. Cl. ..................................... 435/7; 435/188; 435/810; 436/531; 436/533; 436/817; 436/818
[58] Field of Search ........................ 435/7, 21, 28, 188, 435/805, 810; 436/527, 531, 532, 533, 547, 815, 817, 824, 818

[56] References Cited

U.S. PATENT DOCUMENTS 4,214,048  7/1980  Kitagawa ................................. 435/7

OTHER PUBLICATIONS

*Enzyme-Immunoassay*, Maggio (Ed.) (1980), CRC Press, Inc., Fla., pp. 171, 174, 175 and 192.
Schuurs et al., "Clinica Chimica Acta", 81 (1977), pp. 4, 6, 9, 28 and 29.

*Primary Examiner*—Esther M. Kepplinger
*Attorney, Agent, or Firm*—Sughrue, Mion, Zinn, Macpeak and Seas

[57] ABSTRACT

A reagent for use in a "sandwich" enzyme-immunoassay comprising a polymer of a bioactive substance-specific antibody:enzyme conjugate, wherein said antibody is conjugated to said enzyme by means of heterobifunctional cross-linking agent and a "sandwich" enzyme-immunoassay employing the polymer.

9 Claims, 13 Drawing Figures

REAGENT FOR USE IN A SANDWICH SOLID-PHASE ENZYME-IMMUNOASSAY AND PROCESS FOR EMPLOYING SAME

FIELD OF THE INVENTION

The present invention relates to a reagent for use in a "sandwich" solid-phase enzyme-immunoassay and an enzyme-immunoassay employing the same.

BACKGROUND OF THE INVENTION

Routine clinical assessments of endocrine function are currently based on the determination of hormone concentration in blood or urine. Measurement of hormone concentration by radio-immunoassay and radio-receptorassay requires relatively sophisticated and expensive equipment and involves the handling of radioactive materials. Due to the necessary use of radioactivity as well as sophisticated and expensive equipment, the radio-immunoassay cannot be performed in the physician's office or by patients themselves in "do it yourself" tests. By substituting an enzyme for a radioisotope as a marker, most of these problems can be overcome.

"Competitive protein-binding" enzyme-immunoassays for bioactive substance, e.g., hormones, such as human lutropin (hereinafter "LH"), are known (see Fukunaga, T., Rathnam, P., Landesman, R., and Saxena, B.B., *Obstetrics Gynecology*, 61:102 (1983) and Singh, M., Saxena B.B., and Rathnam, P., *Fertility and Sterility*, 41:210 (1984)). In "competitive protein-binding enzyme-immunoassays", the hormone is covalently conjugated with a marker enzyme, e.g., alkaline phosphatase, to yield an "enzyme-labeled hormone" and a hormone-specific antibody is immobilized by, for example, covalently coupling the antibody to glass beads. Increasing concentrations of unlabelled hormones are employed to compete with the "enzyme-labeled hormone" for binding with the antibody. The net amount of the antibody-bound-"enzyme-labeled hormone" is determined by measuring the enzyme concentration colorimetrically.

In "competitive protein-binding" enzyme-immunoassays, a decrease in the amount of antibody-bound-"enzyme-labeled hormone" due to an increase in the concentration of unlabelled hormone results in a proportionate disappearance of color.

"Competitive protein-binding" enzyme-immunoassys are disadvantageous when attempting to visually evaluate the results. That is, it is difficult to visually evaluate the disappearance of color and thus expensive and sophisticated equipment must be employed.

Enzyme-immunoassays which allow for the visual evaluation of an increased color due to increasing concentrations of hormone in the sample are well known and are referred to as "sandwich" enzyme-immunoassays. "Sandwich" enzyme-immunoassays have been extensively used for the determination of the concentration of various drugs and steroids in clinical diagnosis (see Korhonen, M. K. Juntenen, K. O., and Stenman, U. H., *Clinical Chemistry*, 26–13:1829 (1980); Ollerich, M., *Journal Clinical Chemistry Clinical Biochemistry*, 18:197 (1980); and Schneiter, R. S., Lindquist, P., Wong, E. T., Rubensteine, E. E., and Ullmann, E. F., *Clinical Chemistry* 19:821 (1973)).

In the "sandwich" enzyme-immunoassay, the hormone-specific antibody is conjugated with a marker enzyme as opposed to the hormone being conjugated to the enzyme as in a "competitive protein-binding" enzyme-immunoassay. However, the use of such a hormone specific antibody-enzyme conjugate in a "sandwich" enzyme-immunoassay does not provide satisfactory results because it is difficult to obtain a high concentration of the conjugate near the locus of the immobilized hormone-specific antibody to effect bonding without using excessively high concentrations of the antibody conjugate.

The availability of high demand specific antibodies, especially the production of monoclonal, monospecific antibodies together with the "competitive protein-binding" and "sandwich" assays to covalently link enzymes to hormones have permitted the development of enzyme-immunoassays of LH and human chorionic gonadotropin for the detection of ovulation and pregnancy respectively.

More specifically, the concentration of estradiol and LH in serum samples of peripheral blood or urine have been used for the prediction of ovulation (see Fukunaga, T., Rathnam, P., Landesman, R. and Saxena, B. B., *Obstetrics Gynecology*, 61:102 (1983) and Singh, M., Saxena, B. B. and Rathnam, P., *Fertility and Sterility*, 41:210 (1984)). The results indicate that a 50% increase in the midcycle LH surge of the mean basal level of plasma LH is one of the best hormonal indices of impending ovulation which may occur between 24 to 56 hours after the rise in LH. This has been difficult to measure in the urine by the conventional "sandwich" assay and the present invention overcomes this problem.

Due to their lack of sensitivity, immunological tests utilizing the principle of hemagglutination inhibition or latex agglutination inhibition have not permitted the detection of the midcycle pre-ovulatory LH surge. Although radio-immunoassays provide the required higher sensitivity to detect mid-cycle LH surge in the urine and blood, such assays again require expensive and sophisticated equipment.

The clinical validation of the conventional "competitive protein-binding" enzyme-immunoassay of LH in the detection of pre-ovulatory LH surge in the urine, where the LH surge was validated by the occurrence of follicular rupture within 12 to 24 hours after the surge, and substantiated with other parameters such as the thermal shift in the BBT, spinenbarkeit of the cervical mucus, hormonal levels in serum or urine and ultrasonography, has been shown in Singh, M., Saxena, B. B. and Rathnam, P., *Fertility and Sterility*, 41:210 (1984)). The present invention considerably improves the mode of detection of the LH.

The enzyme-immunoassay of the present invention offers the sensitivity of a radio-immunoassay while preserving the simplicity of collection of urine samples. The sensitivity of the enzyme-immunoassay of the present invention is equal to that of the radio-immunoassay and is almost 10-fold higher than the hemagglutination inhibition assay. Further, the enzyme-immunoassay of the present invention requires less than 90 minutes and the end point, as indicated by appearance of color, is easy to interpret.

When applied to the measurement of LH in the urine, the present invention provides a rapid and reliable aid to detect pre-ovulatory LH surge to predict ovulation in women. Such a measurement is extremely useful in the management of infertility and dating the time for artificial insemination and in the selection for optimum time to aspirate mature ova for in vitro fertilization as well as in aiding women in natural family planning by abstinence during the fertile period.

SUMMARY OF THE INVENTION

Accordingly, an object of the present invention is to provide a reagent for use in a "sandwich" enzyme-immunoassay which simply and economically allows for a highly sensitive determination of concentrations of bioactive substances such as hormones.

Another object of the present invention is to provide a "sandwich" enzyme-immunoassay employing such a reagent.

The above objects of the present invention have been met by:
a reagent for use in a "sandwich" enzyme-immunoassay comprising a polymer of a bioactive substance-specific antibody:enzyme conjugate, wherein said antibody is conjugated to said enzyme by means of a heterobifunctional cross-linking agent.

In another embodiment of the present invention, the above objects have been met by a "sandwich" enzyme-immunoassay comprising the steps of:

(1) immobilizing an antibody specific to the bioactive substance to be assayed on a substrate;

(2) incubating the immobilized bioactive substance-specific antibody with the sample to be assayed;

(3) adding a reagent comprising a polymer of a bioactive substance-specific antibody enzyme conjugate with the product of step (2), wherein said antibody is conjugated to said enzyme by means of a heterobifunctional cross-linking agent;

(4) removing the unbound polymer of bioactive substance-specific antibody:enzyme conjugate from the product of step (3); and (5) assaying for the enzyme in the resulting conjugate of step (4).

In a further embodiment of the present invention, the above objects have been met by a "sandwich" enzyme immunoassay comprising the steps of:

(1) immobilizing an antibody specific to the bioactive substance to be assayed on a substrate;

(2) simultaneously incubating the immobilized bioactive substance-specific antibody with the sample to be assayed and a reagent comprising a polymer of a bioactive substance-specific antibody:enzyme conjugate, wherein said antibody is conjugated to said enzyme by means of heterobifunctional cross-linking agent;

(3) removing the unbound polymer of bioactive substance-specific antibody:enzyme conjugate from the product of step (2); and (4) assaying for the enzyme in the resulting conjugate of step (3).

DETAILED DESCRIPTION OF THE INVENTION

Figure 1:
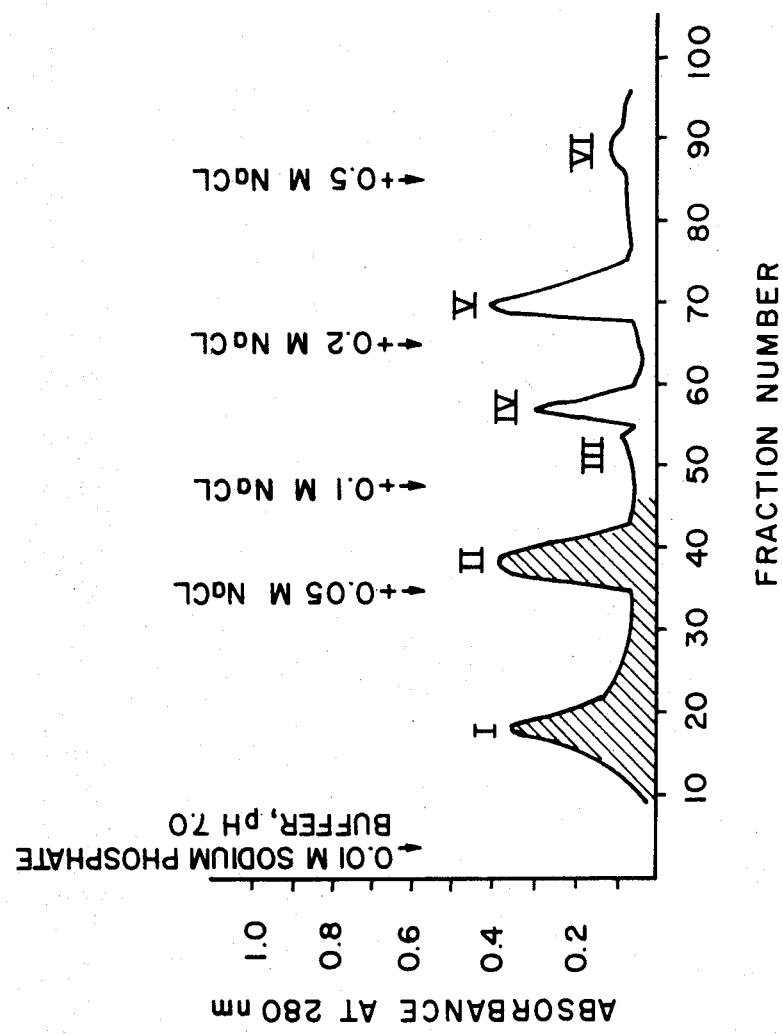
FIG. 1: Ion-exchange chromatography of the γ-globulin fraction on a 2×30 cm column of DE-52 cellulose. Buffer: 0.01M sodium phosphate, pH 7.0. Flow rate: 15 ml/10 min/fraction. The hatched area depicts the LH-specific-γ-globulin-containing fractions.

As stated above, the present invention relates to a reagent for use in a "sandwich" enzyme-immunoassay comprising a polymer of bioactive substance-specific antibody: enzyme conjugate, wherein said antibody is conjugated to said enzyme by means of a heterobifunctional cross-linking agent.

The bioactive substance employed in the present invention can be a hormone, drug, or any other substance which has biological activity, e.g., LH, hCG, TSH, or FSH.

The enzyme employed in the present invention can be any well-known enzyme marker employed for "sandwich" enzyme-immunoassays such as alkaline phosphatase and horse radish peroxidase.

The bioactive substance-specific antibody can be prepared by well-known means.

An example of the heterobifunctional cross-linking agent which can be employed in the present invention is m-maleimidobenzoyl N-hydroxy-succinimide ester (hereinafter "MBS") obtained from Pierce Chemical Co.

Monomers of the bioactive substance-specific antibody:enzyme conjugate can be polymerized to form a polymer thereof by means of polymerizing agents such as glutaraldehyde or carbodimide.

Samples to be assayed in the present invention are typically derived from body fluids, for example, blood, urine, serum or spinal fluid.

The bioactive substance-specific antibody can be immobilized by well-known means, such as absorption or covalent linkage, on a substrate such as polystyrene tubes, polystyrene beads, glass beads, powder or sticks.

Polystyrene beads generally provide a more uniform coating and consequently higher reproducibility as compared to glass beads to which antibody was covalently linked via amino groups (see Fukunaga, T. Rathnam, P., Landesman, R. and Saxena, B. B., *Obstetrics Gynecology* 61:102 (1983)). The use of a solid phase provides the separation of unreacted, excess reagents or undesirable interfering proteins in the body fluid sample and avoids their interference during the next step of the reaction. Also, in the assay of the present invention, the body fluid sample first reacts with the antibody on the solid phase and is then removed, thus there is no interference of urine during the step (2), whereas in the liquid radio-immunoassay system, the body fluid is present throughout the incubation period. The use of immuno-globulin purified from the antisera eliminates the absorption of other serum proteins to the solid phase, thus enhancing the sensitivity, specificity and speed of binding.

The particular assay employed for measuring the concentration of the enzyme will, of course, depend upon the enzyme employed. For example, a colorimetric assay for determining the concentration of alkaline phosphatase is disclosed in Fukunaga, T. Rathnam, P., Landesman, R. and Saxena, B. B., *Obstetrics Gynecology* 61:102 (1983).

The following example is provided for illustrative purposes and is in no way intended to limit the scope of the present invention.

EXAMPLE

1. Preparation and Purification of γ-Globulin Fraction From Antiserum Against Human Pituitary LH A 200 mg/l solution of human pituitary Lh was emulsified in physiological saline with an equal volume of Fruend's complete adjuvant. One ml of this suspension was then injected at multiple sites, once a week, into each of six rabbits. Serum from blood samples, from ear veins of each rabbit, was tested for specific binding of $^{125}$I-labeled LH every four weeks. When the antiserum from a rabbit showed high affinity and high titer in such a test, the rabbit was bled once a month to obtain 25 to 50 ml of blood. The γ-globulin in the sera was separated by precipitation in most of the other blood proteins with Rivanol, a lectic acid (1:1) compound with 6,2-diaminio-2-ethoxyacridine (see Horejsi, J. and Smetana, R., *Acta Med. Scand.* 155:65 (1956)). The γ-globulin fraction was gel-filtered on a column of Sephadex G-50 equilibrated with 0.1M ammonium bicarbonate buffer, pH 8.5. The garnna-globulin fractions precipitated by Rivanol from the "medium" and "high" titer antiseria yielded similar binding capacities in the range of $339-381 \times 10^{-6}$ μg of $^{125}$I-labeled human LH/μg protein, indicating that the isolation of immune γ-globulin would permit the use of antisera with varying titers as shown in Table 1 below.

TABLE 1
YIELD AND ACTIVITY OF THE SPECIFIC ANTI-GLOBULIN AND ITS CONJUGATE WITH ALKALINE PHOSPHATASE

| Fraction | Protein | Total Protein | Binding Capacity × 10$^6$ $^{125}$I-Labeled LH Bound/μg of Protein |
|---|---|---|---|
| "High"-Titer Antiserum | 3.2 g | | 525.6 |
| "Medium"-Titer Antiserum | 1.8 g | 5.0 g | 239.5 |
| γ-Globulin Fraction | | | |
| From "High" Antiserum | 375 mg | | 338.8 |
| From "Medium" Antiserum | 276 mg | 651 mg | 380.5 |
| Anti-LH-γ-Globulin | 398 mg | | 2247.1 |
| MBS-Derivative | | | 1364.3 |
| SG-75 Fraction | 7.0 mg$^a$ | | 1367.5 |
| Polymer$^b$ | 1.8 mg$^a$ | | 349.0 |

$^a$From 10 mg of antibody.
$^b$The enzyme content was 0.2 mg/mg polymer = 4.25 units/mg polymer.

Next, the γ-globulin fraction was purified by ion-exchange chromatography on DE-52 cellulose (Whatman Ltd.). More specifically, 500 mg (in terms of protein) of the γ-globulin fraction was dialyzed overnight against 0.01M sodium phosphate buffer, pH 7.0. The dialysand was applied to a 2×30 cm column of DE-52 cellulose that had been equilibrated in the same buffer. After the unabsorbed fraction had been washed through, the column was successively eluted with the same sodium phosphate buffer containing 0.05, 0.2 and 0.5M NaCl. 15 ml fractions were collected and pooled according to their absorbance at 280 nm (see FIG. 1). Portions of each fraction were tested for specific binding with $^{125}$I-labeled LH. As shown by the hashed region in FIG. 1, Fractions I and II contained the LH-specific antibodies.

As shown in Table 1 above, the fractionation of the γ-globulin fraction by ion-exchanged chromatography on DE-52 cellulose increases the binding capacity to $2247 \times 10^{-6}$ μg of $^{125}$I-labeled LH and yields a considerably purified antibody in Fractions I and II (see FIG. 1). Thus, the preparation of the high titer and affinity γ-globulin of the LH-specific antibody avoided the enzyme-labeling of other inert or non-immune γ-globulins in the antisera. The use of the purified antibody also minimized nonspecific binding in the control samples, i.e., in the absence of LH, and thus enhanced the rate of the reaction.

2. Preparation and Purification of LH-Specific Antibody: Enzyme Conjugate

Fraction II in FIG. 1 was used to conjugate with alkaline phosphatase. The alkaline phosphatase (Type VIIS containing 2200 International units/mg, Sigma Chemical Co.) was stored at 4° C. p-Nitrophenyl phosphate, disodium (Sigma Chemical Co.) was used as the substrate in the colorimetric assay of the enzyme, in accord with the manufacturer's instructions.

More specifically, 10 mg of the anti-LH-γ-globulin was dissolved in 1.0 ml of 0.1M sodium phosphate buffer pH 7.0, containing 0.05M NaCl. A 25 μl aliquot of 1,4-dioxane containing 0.53 mg of MBS was added to the mixture, which was allowed to react for 1.0 hour at 30° C. on a shaker. Then, the mixture was gel-filtrated on a 1×60 cm column of Sephadex G-25 (Medium) equilibrated with 0.1M sodium phosphate buffer pH 7.0, containing 0.01M MgCl$_2$ and 0.05M NaCl. The column was eluted with the same buffer at a flow rate of 1.1 ml/10 min/fraction. The results are shown in FIG. 2.

Figure 2:
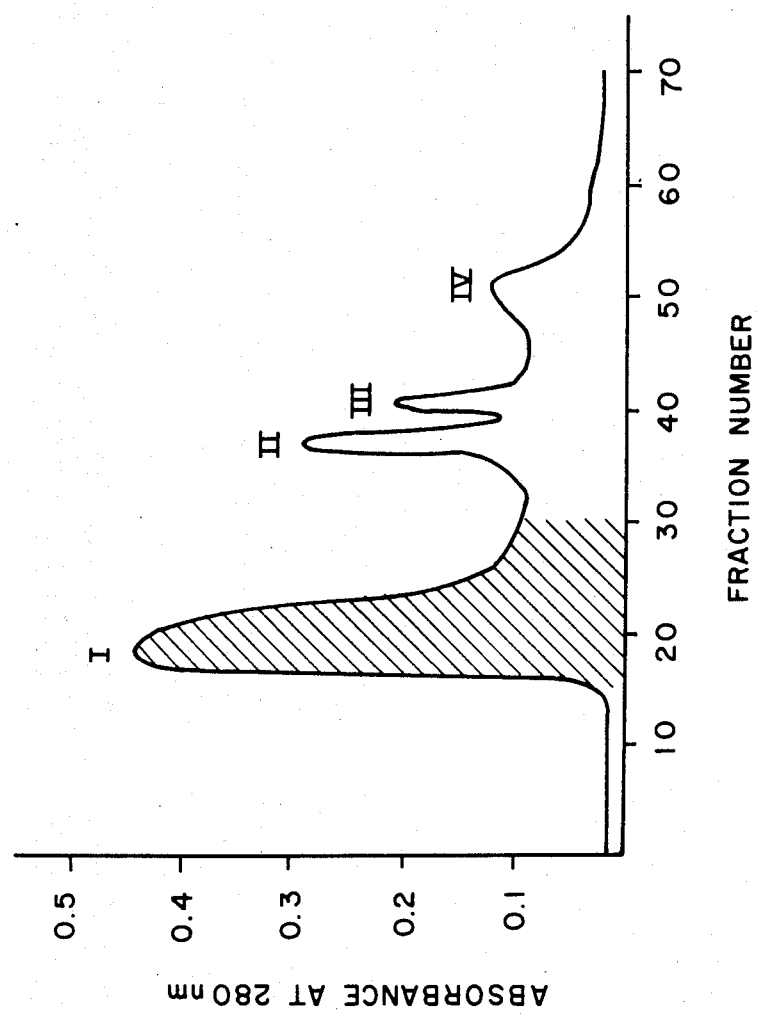
FIG. 2: Gel-filtration of the MBS-treated anti-LH-γ-globulin on a 1×30 cm column of Sephadex G-25 (Medium). Buffer: 0.1M ammonium bicarbonate, pH 8.5. Flow rate: 1.1 ml/10 min/fraction. The MBS-derivative eluted in the fractions is shown by the hatched area.

The unretarded fraction, i.e., Fraction I in FIG. 2, containing the MBS derivative of the anti-LH-γ-globulin was immediately pooled and reacted with 1.0 mg of alkaline phosphate for 1.0 hour at 30° C. (antibody:enzyme ratio=10:1 (w/w). Preliminary studies indicated that this ratio was better than a ratio of 2:1, 5:1, and 20:1. The reaction was then stopped by the addition of 100 μl of 1.0M 2-mercaptoethanol to yield a final concentration of 0.01M 2-mercaptoethanol.

The LH-specific antibody:enzyme conjugate was purified by gel-filtration on a 1×150 cm column of Sephadex G-75 (Superfine) in 0.01M sodium phosphate buffer, pH 7.0, containing 0.01M $MgCl_2$ and 0.05M NaCl and the column was eluted with the same buffer at a flow rate of 1.0 ml/20 min/fraction. The results are shown in FIG. 3.

Figure 3:
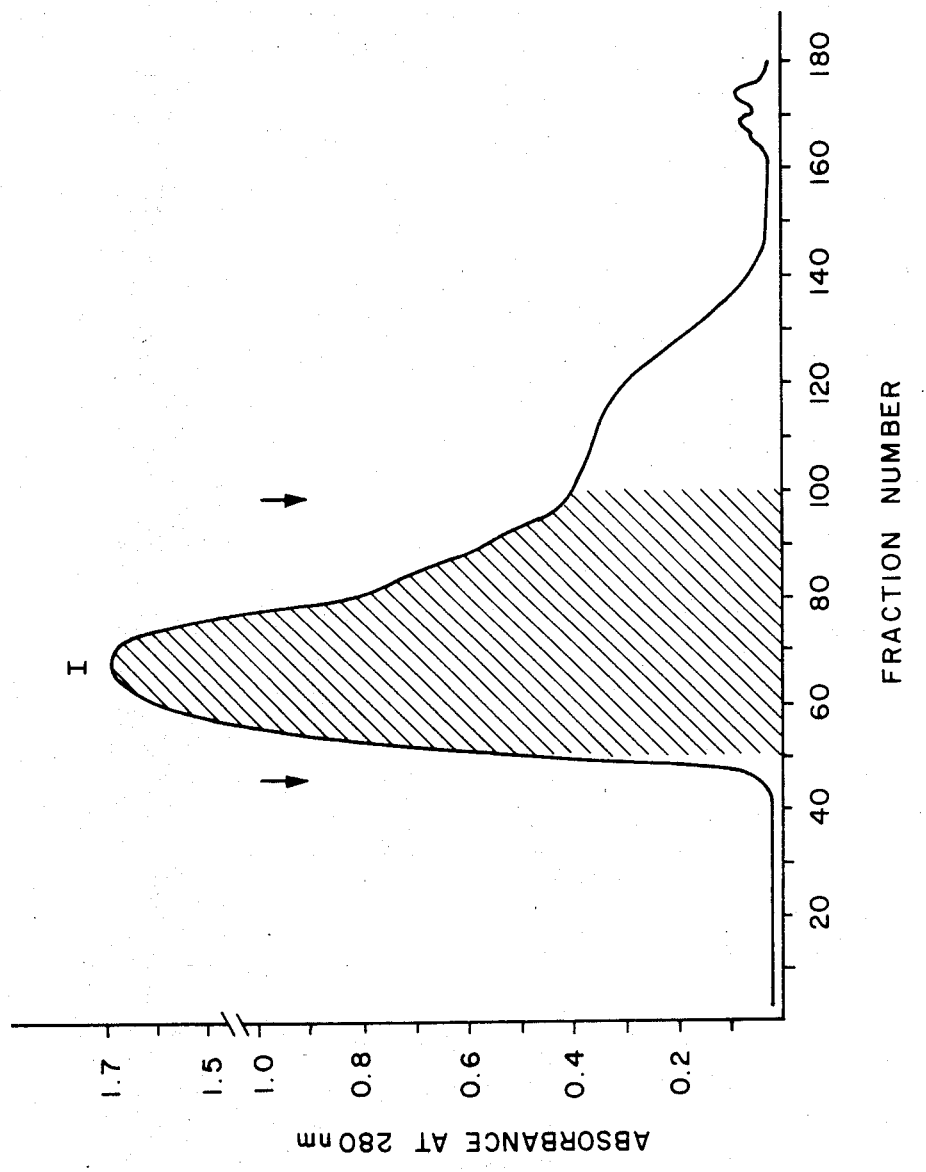
FIG. 3: Gel-filtration of the MBS-derivative of the anti-LH-γ-globulin after incubation with alkaline phosphate, on a 1×150 cm column Sephadex G-75 (Superfine). Buffer: 0.01M sodium phosphate buffer, pH 7.0. Flow rate: 1 ml/20 min/fraction. The hatched area contained both antibody and enzyme activities.

The fractions shown in FIG. 3 were analyzed for protein content, enzyme activity and for their specific binding with $^{125}$I-labelled LH. As FIG. 3 illustrates, the conjugate of the LH-specific antibody and enzyme was recovered in Fraction I.

As shown in Table 1 above, the MBS-derivative of the antibody showed a slight decrease in its binding capacity to $^{125}$I-labeled LH. Fraction I containing the conjugate, consisted of 7.1 mg of protein in a volume of 18 ml.

3. Polymerization of LH-specific Antibody:Enzyme Conjugate and Purification of Polymer Thereof Fraction I, as shown in FIG. 3, was added to 142 μl of a 250 g/l glutaraldehyde solution in water to yield a final concentration of 2.0 g/l of glutaraldehyde so as to polymerize the LH-specific antibody:enzyme conjugate monomers. The reaction was allowed to proceed for 3.0 hours at room temperature. The reaction mixture was concentrated with stirring in a 50 ml Amicon Ultrafilter with a PM-10 filter to a volume of 10 μl, equilibrated 3 times in 0.01M sodium phosphate buffer, pH 7.0 and reconcentration to a final volume of 8.2 ml. The protein concentration was an important factor during the polymerization step with glutaraldehyde. Two high a protein concentration during the polymerization step with glutaraldehyde lead to the formation of precipitates which resulted in a considerable decrease in the yield of the conjugates. However, if the concentration was in the range of 0.1 to 0.2%, precipitation did not occur and the yield of the conjugate was adequate.

Figure 4:
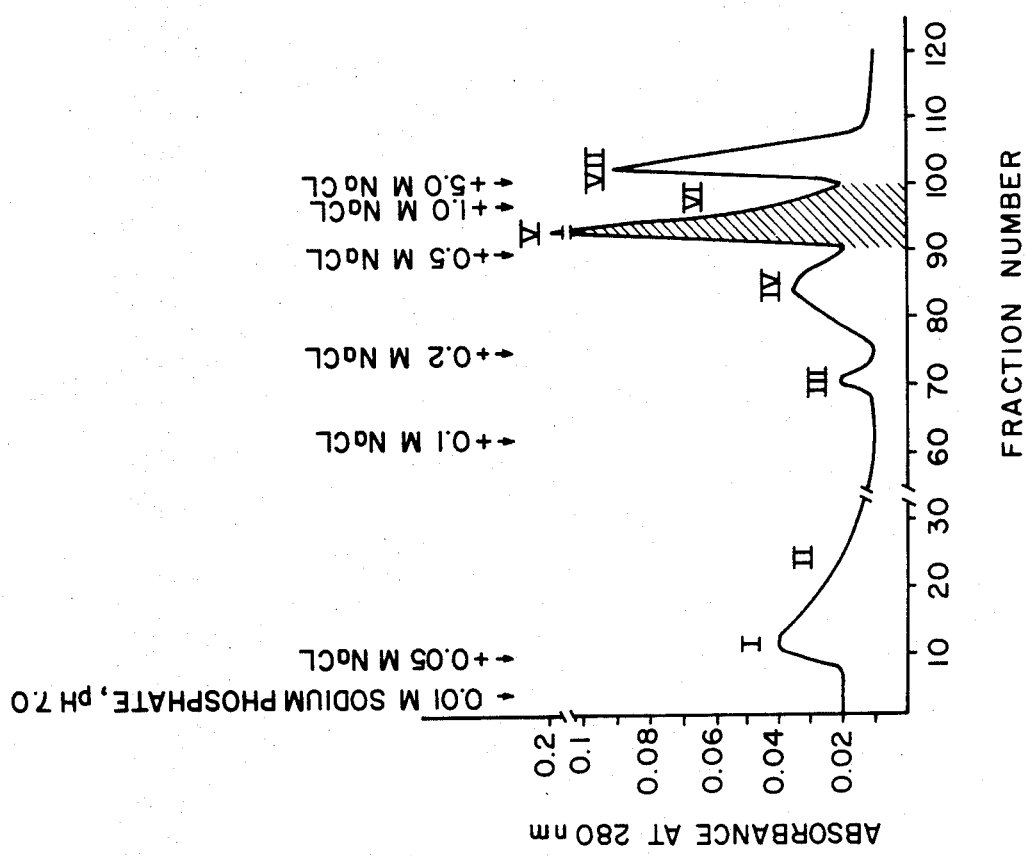
FIG. 4: Ion-exchange chromatography of Fraction I from the Sephadex G-75 (Fine) column (FIG. 3) on a 1×30 cm column of DE-52 cellulose. Buffer: 0.01M sodium phosphate buffer, pH 7.0. Flow rate: 2 ml/min fraction. The hatched area contained the conjugate.

In order to separate the monomers from the polymers, the polymer was purified by means of ion-exchange chromatography on a 1×30 cm of DE-52 cellulose (see FIG. 4). The column was eluted with 0.01M sodium phosphate buffer pH 7.0, by a stepwise gradient of 0.05, 0.1, 0.2, 0.5 and 1.0M NaCl in the above buffer. The fractions were then pooled and dialyzed overnight against the same phosphate buffer to remove excess NaCl and excess reagents.

As shown in FIG. 4, Fraction V, eluted with the buffer containing 0.5M NaCl, contained the polymer. Fraction V contained 1.8 mg of protein in a volume of 1.5 ml.

As shown in Table 1 above, the binding capacity of the polymer was $349 \times 10^{-6}$ μg human LH/μg protein and 20 μg of enzyme per 100 μg of polymer. The validity of the fraction being a polymer and not a mixture of antibody and enzyme was confirmed by testing Fraction V in both the enzyme-immunoassay and radioimmunoassays described in Fukunaga, T., Rathmann, P., Landesman, R., Saxena, B. B., *Obstetrics Gynecology* 61:102 (1983) and Singh, M., Saxena, B. B., and Rathman, P., *Fertility and Sterility*, 41:210 (1984). The other fraction also contain conjugates of the antibody and enzyme of varying ratios, however, Fraction V was the best for enzyme-immunoassay.

The polymer was tested for sterility after storage in a refrigerator at 4° C. in the presence of 1.0 g/l BSA and 0.1 g/l sodium azide over a period of time. The polymer was found to be stable up to a 3-month period. The slight loss of enzyme activity could be compensated up to 6 months by increasing the dose levels of the polymer without affecting the quality of the enzyme-immunoassay. The enzyme component of the polymer, however, lost significant activity if the polymer was lyophilized.

4. Preparation of LH-specific Antibody Coating Polystrene Beads and Tubes

Antibody coated polystyrene beads were prepared in the following manner. Polystyrene beads of ¼" diameter (Polysciences, Inc.) were used for coupling with the purified LH-specific antibody. The beads were washed in tap water for 1.0 hour, rinsed 3 times with distilled water, and then washed with a solution of 9.0 g/l NaCl in a glass trough for 3.0 hours at room temperature on a shaker. The beads were incubated with a 2.0 g/l glutaradehyde solution in 0.01M phosphate buffer pH 7.0, for 2.0 hours at room temperature on a shaker. The solution was decanted and the beads were washed thoroughly 6 times with excess of the same phosphate buffer to remove any residual glutaraldehyde. The beads were then incubated in a 0.035 g/l solution of the LH-specific antibody in the phosphate buffer, for 1.0 hour at room temperature, and then left overnight at 4° C. on a rotary shaker at slow speed in order to expose the entire surface of the beads to the LH-specific antibody solution. The beads were then removed from the LH-specific antibody solution and stored at 4° C. in sodium phosphate buffer, pH 7.0 containing 1.0 g/l sodium azide. The beads were tested for binding with $^{125}$-labeled LH to check the efficiency of coating with the LH-specific antibody to determine the binding capacity by Scatchard analysis (see Scatchard, G., *Ann. New York Academy Science*, 51:660 (1949)). The polystyrene beads coupled to the antibody were found to have a binding capacity of $531.5 \times 10^{-6}$ μg human LH/bead.

Antibody coated polystyrene tubes were prepared in essentially the same manner as were the antibody-coated polystyrene beads. More specifically, 10×75 mm polystyrene tubes were first rinsed several times with distilled water and then 500 μl of a solution of 9.0 g/l NaCl were added to each tube. The tubes were allowed to stand for 3.0 hours at room temperature with gentle shaking, washed 3 times with distilled water, and then activated by incubation with 500 μl per tube of a 12.5 g/l glutaraldehyde solution in 0.01M sodium phosphate buffer, pH 7.0, for 2.0 hours, at room temperature. The tubes were thoroughly rinsed to remove any residual glutaraldehyde. Each tube was first incubated with 500 μl of a 0.15 g/l solution of the anti-γ-globulin in sodium phosphate buffer, pH 7.0, for 1.0 hour, at room temperature, on a shaker, and then left overnight at 4° C. The polystyrene tubes coupled to the antibody showed a binding capacity of $424.9 \times 10^{-6}$ mg human LH per tube. The antibody coated beads and tubes were stable for at least 6 months, if stored in sodium phosphate buffer, pH 7.0 at 4° C. However, they lost activity if they were dry.

The polystyrene tubes were better in performance and were easier to handle than polystrene beads to perform the enzyme-immunoassay. The steps required were only to get the liquid from the tubes, whereas with the polystrene beads, a net was required to retain the beads inside the tubes.

The protocol for the enzyme-immuno assay employing sequential incubation, i.e., first incubating the samples in the presence of the immobilized antibody and then adding the antibody-enzyme polymer using polystyrene beads and polystyrene tubes is shown in Tables 2 and 3, respectively, below.

TABLE 2
PROTOCOL FOR "SANDWICH" ENZYME-IMMUNOASSAY FOR BEADS
(Sequential Incubation)

| | Standard or Sample[2] 1:5 Dilution | Control Urine[3] | Anti-LH-γ-Globulin-Alkaline Phosphatase Polymer[4] | RIA Buffer |
|---|---|---|---|---|
| Blank[1] | | 400 μl | 200 μl | 200 μl |
| LH Standards 0-200 | | | | 0 μl |
| Int. Units/l | 200 μl | | 200 μl | 200 μl |
| Sample | 200 μl | | 200 μl | 200 μl |

Rinse Anti-LH-γ-globulin-coated beads with distilled water and add 1 bead to each tube. Incubate 1.0 hour at 37° C. Decant and wash 3 times with 2.0 ml of distilled water, each time.
Add 50 μl diethanolamine substrate solution, pH 9.8. Incubate for 30 minutes at 37° C. Add 250 μl 1.0 N NaOH. Measure absorbance at 420 nm in a Digispec.

[1]Prepared in BSA-coated, 10 × 75 mm polystyrene tubes prepared by the addition of 500 μl of a 20 g/l solution of BSA to each tube. After 1.0 hour, the BSA solution was decanted and the tubes were turned upside down for 15-30 minutes todrain the solution and dry the tubes. The tubes were then washed with 1.0 ml distilled water and turned upside down to drain and dry. The BSA-coated tubes were stored at 4° C. in a dessicator.
[2]Unknown urine samples diluted 1:5 with radio-immunoassay Buffer comprising 0.05 M sodium phosphate buffer, pH 7.2 containing 1.0 g/l BSA and 0.1 g/l sodium azide (herinafter "RIA Buffer").
[3]Normal urine diluted 1:5 with RIA Buffer.
[4]Antibody-enzyme polymer, diluted in RIA Buffer, according to a predetermined amount.

TABLE 3
PROTOCOL OF "SANDWICH" ENZYME-IMMUNOASSAY FOR TUBES
(Sequential Incubation)

| Ab-Coated Tubes[1] | Standard or Sample[2] 1:5 Dilution | Control Urine[3] 1:5 Dilution | Anti-LH-γ-Globulin-Alkaline Phosphatase Polymer[4] | RIA Buffer |
|---|---|---|---|---|
| Blank[1] | | 400 μl | 200 μl | 400 μl |
| LH Standards 0-200 | | | | 0 μl |
| Int. Units/l | 200 μl | 200 μl | 200 μl | 200 μl |
| Sample | 200 μl | 200 μl | 200 μl | 200 μl |

Incubate 1.0 hour at 37° C. Wash 3 times as before.
Add 50 μl of diethanolamine substrate solution, pH 9.8. Incubate for 30 minutes at 37° C. Add 250 μl of 1.0 N NaOH. Measure absorbance at 420 nm in a Digispec.

[1]Prior to use, remove anti-LH-γ-globulin solution from tubes and rinse tubes with distilled water.
[2]Unknown urine samples diluted 1:5 with RIA Buffer.
[3]Normal urine diluted 1:5 with RIA Buffer.
[4]Antibody-enzyme polymer diluted in RIA Buffer, according to a predetermined amount.

The protocols for the enzyme-immunoassay employing simultaneous incubation of the sample and the enzyme-antibody polymer using polystyrene beads and polystyrene tubes is shown in Tables 4 and 5, respectively, below.

TABLE 4
PROTOCOL FOR "SANDWICH" ENZYME-IMMUNOASSAY FOR BEADS
(Simultaneous Incubation)

| | Standard or Sample[2] | Anti-LH-γ-Globulin-Alkaline Phosphatase Polymer[3] | Control Urine[4] | RIA Buffer |
|---|---|---|---|---|
| Blank[1] | | 100 μl | 200 μl | 100 μl |
| LH Standard[5] (200 Int. units/l) | 200 μl | 100 μl | | |
| Sample | 200 μl | 100 μl | | |

Rinse Anti-LH-γ-globulin-coated beads with distilled water and add 1 bead to each tube. Incubate for 1.0 hour at 37° C. Decant and wash 3 times with 2 ml of distilled water, each time.
Add 50 μl of diethanolamine substrate solution. Incubate 30 minutes at 37° C. Add 250 μl of 1.0 N NaOH. Measure absorbance at 420 nm in a Digispec.

[1]Prepared in BSA-coated, 10 × 75 mm polystyrene tubes. Prepared by the addition of 500 μl of a 20 g/l solution of BSA to each tube. After 1.0 hour, the BSA solution was decanted and the tubes were turned upside down for 15-30 minutesto drain the solution and dry the tubes. The tubes were then washed with 1.0 ml distilled water and turned upside down to drain and dry. The BSA-coated tubes were stored at 4° C. in a dessicator.
[2]Unknown urine sample diluted 1:5 with RIA Buffer.
[3]Polymer diluted in RIA Buffer, according to a predetermined amount.
[4]Normal urine diluted 1:5 with RIA Buffer.
[5]Made in control urine.

TABLE 5
PROTOCOL FOR "SANDWICH" ENZYME-IMMUNOASSAY FOR TUBES
(Simultaneous Incubation)

| Anti-LH-γ-Globulin-Coated Polystyrene Tubes[1] | Standard or Sample[2] | Anti-LH-γ-Globulin-Alkaline Phosphatase Polymer[3] | Control Urine[4] | RIA Buffer |
|---|---|---|---|---|
| Blank | | | 200 μl | 200 μl |
| LH Standards[5] (200 Int. units/l) | 200 μl | 200 μl | | |
| Sample | 200 μl | 200 μl | | |

Incubate 1.0 hour at 37° C. Decant and wash 3 times with 2.0 ml of distilled water
Add 50 μl of diethanolamine solution and incubate 30 minutes at 37° C. Add 250 μl of 1.0 N NaOH and measure absorbance at 420 nm in a Digispec

[1]Prior to use, remove anti-LH-γ-globulin from tubes and rinse tubes with distilled water.
[2]Unknown urine sample diluted 1:5 with RIA Buffer.
[3]Polymer diluted in RIA Buffer, according to a predetermined amount.
[4]Normal urine diluted 1:5 with RIA Buffer.
[5]Made in control urine.

Figure 5:
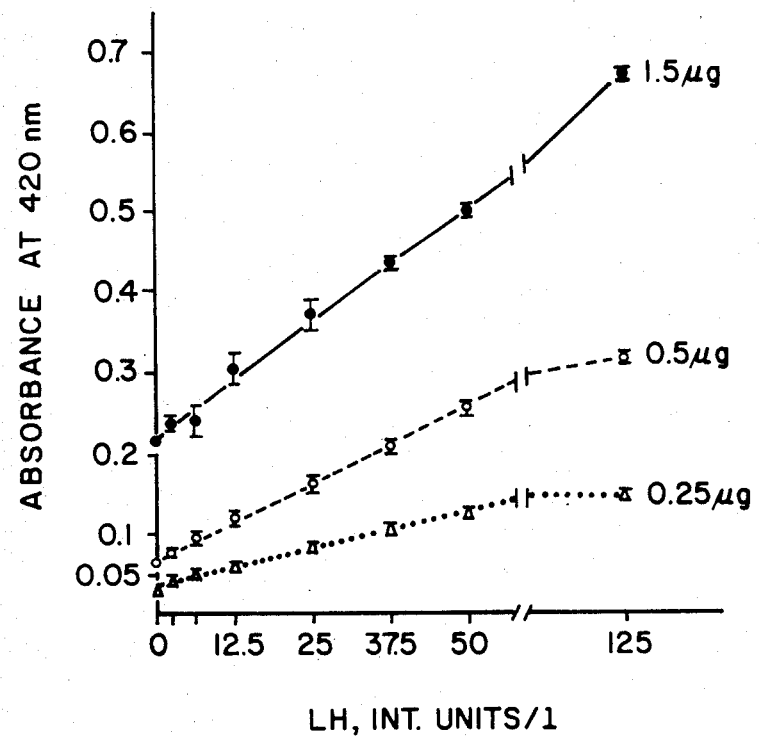
FIG. 5: Enzyme-immunoassay using varying levels of the reagent of the present invention. Polystyrene beads were used for the solid phase and sequential incubation was performed.

The reagent of the present invention was tested at various concentrations to determine the optimum level to yield optimum color, i.e., little color at 0 ng LH/ml and maximum color at approximately 50% increase in the rise of ovulatory LH surge, i.e., 30 to 50 Int. units/l, which is approximately 5 to 10 fold higher than the basal levels of LH during follicular and luteal phases of the menstrual cycle. As FIG. 5 demonstrates, the color increased linearly with increasing doses of LH from 2.5 to 500 Int. units/l. At dose levels of 1.5, 3.0 and 7.5 μg, the conjugate showed high "blank" with 0 Int. units/l. At the 0.25 μg level, the "blank" was low but the sensitivity was poor. At 0.5 μg of the reagent of the present invention, the "blank" was low with a good color increase between 2.5 to 500 Int. units/l. Thus, 0.5 μg was chosen as the optimum dose of this batch of polymer for use in an enzyme-immunoassay. Similarly, each new batch was examined to adjust the dose level of the polymer for optimum performance in the enzyme-immunoassary.

For qualitative analysis, the polymer was tested once a month for optimum levels and, if necessary, the quantity was adjusted so that at basal levels of LH, there was little yellow color. At the "ovulatory" levels of LH, the color development was quite distinct.

Figure 6:
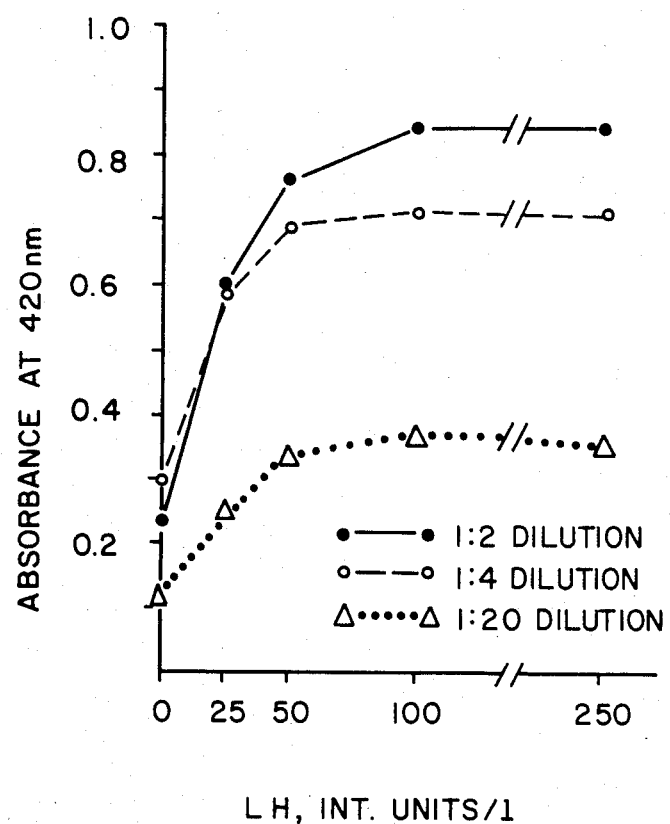
FIG. 6: Colorimetric determination of alkaline phosphatase in the reagent of the present invention, using varying dilutions of enzyme substrate solution. A total volume of 200 μl of enzyme substrate solution was added to each tube.

In order to choose the optimum concentration of the substrate for the colormetric determination of the alkaline phosphatase, the enzyme substrate solution, prepared according to the supplier (Sigma Chemical Co.) was tested with dilutions of 1:2, 1:4 and 1:20. As shown in FIG. 6, the optimum concentration of the enzyme substrate solution was at a 1:2 dilution, as shown by the maximal and linear color levels obtained between 0 and 500 Int. units/l levels. The 300 μg volume of substrate yielded similar but lower absorbancies.

Figure 7:
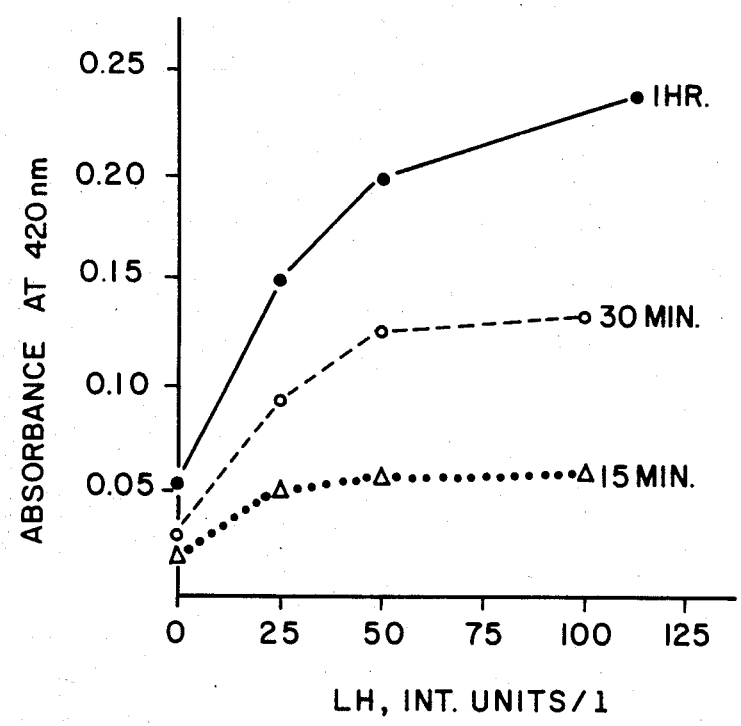
FIG. 7: Colorimetric determination of alkaline phosphatase in the reagent of the present invention using various incubation times with the enzyme substrate solution.

The optimum time of incubation with the enzyme substrate solution was determined and the results are shown in FIG. 7. More specifically, at 37° C., the color increased proportionally with increasing incubation periods of 15 minutes, 30 minutes and 1 hour. The color was maximal at 1 hour of incubation. However, in order to reduce the total time of the performance of the assay, a 30 minute incubation time was selected for routine enzyme-immunoassay procedures.

Figure 8:
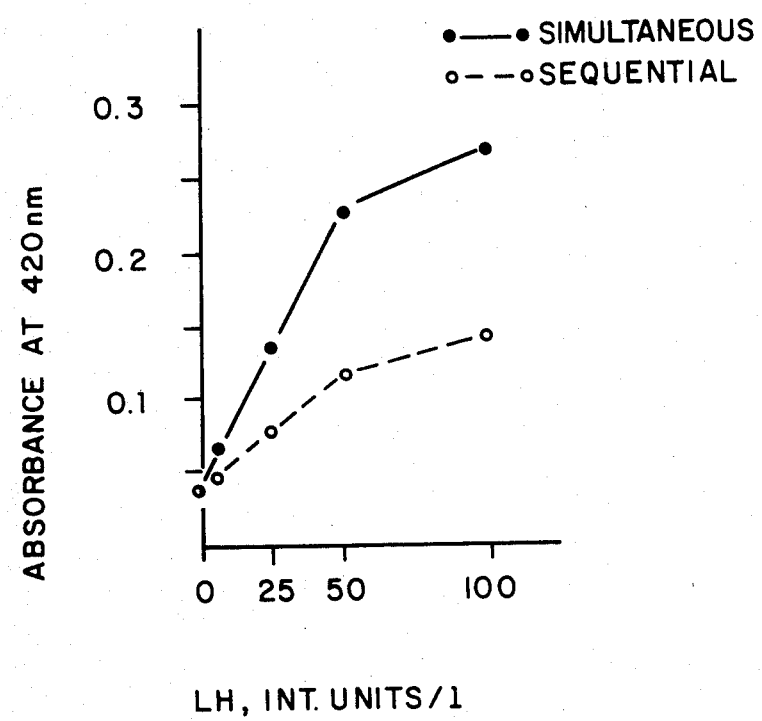
FIG. 8: Comparison of the simultaneous versus sequential incubation assay embodiments of the present invention. A total volume of 300 μl of enzyme substrates solution was added to each tube.

FIG. 8 shows a comparison of results achieved between the "simultaneous incubation" and the "sequential incubation" in total incubation volumes of 300 μl. As FIG. 8 demonstrates, the simultaneous incubation of the solid-phase-antibody with a hormone and with the polymer of the present invention proved to be very effective in shortening the total time of the performance of the enzyme-immunoassay procedure, but also gave increased color development. A comparison of the simultaneous versus sequential incubation procedures use of a total incubation volume of 400 μl yielded a similar trend of results to that of the 300 μl volume, however, a lower color intensity was observed.

Figure 9:
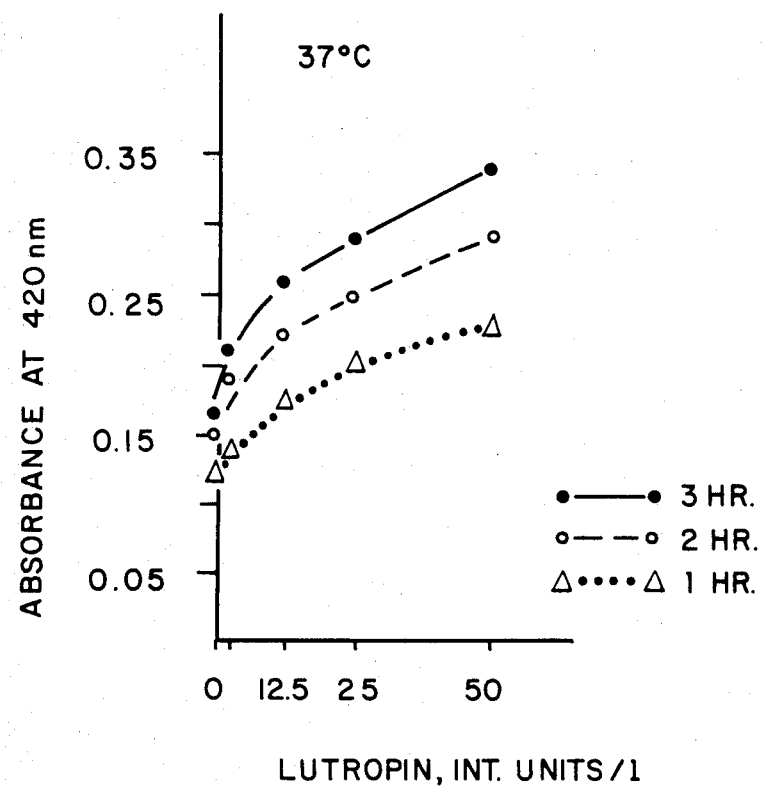
FIG. 9: Simultaneous incubation with polystyrene beads for varying times at 37° C.

The effect of incubation times and temperature on antibody-hormone binding in a simultaneous incubation is shown in FIG. 9. As the results in FIG. 9 demonstrate, incubations of the antibody, hormone and polymer simultaneously at room temperature and at 37° C. for various times, increased the color with temperature and time, indicating increased binding of the polymer and hormone. Incubation at 37° for 1.0 hour is optimum which also reduces the total time of the enzyme-immunoassay performance. At room temperature, the incubation had to be extended for an additional hour to achieve the same results.

Figure 10:
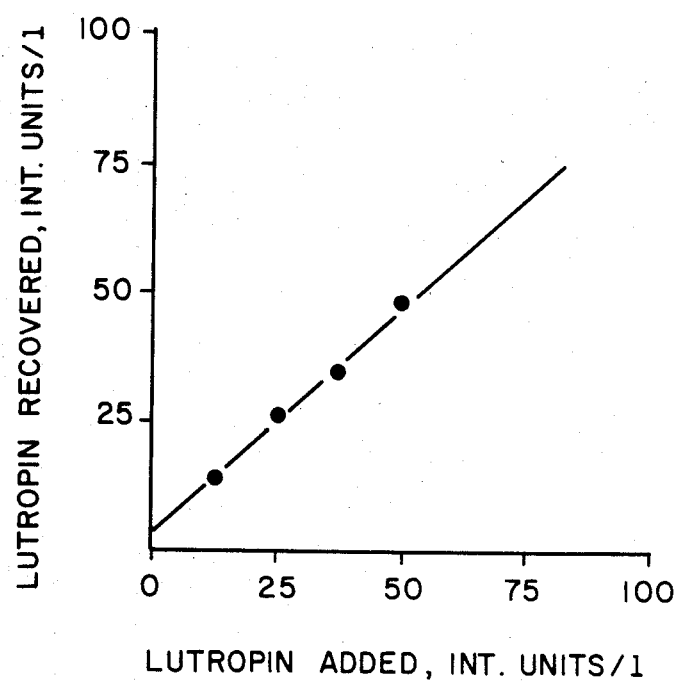
FIG. 10: Recovery of known amounts of LH in enzyme-immunoassay. Tubes were used with sequential incubation. The LH was added in 1:5 diluted urine.

The reproducibility and reliability of the enzyme-immunoassay of the present invention was established by a determination of the percent recovery of known amounts of LH added to the urine samples and to the solutions prior to the assay. The results are shown in FIG. 10 wherein from 88 to 92% recoveries of the known amounts of the hormone added to the urine samples and assayed in the enzyme-immunoassay of the present invention were obtained.

Figure 11:
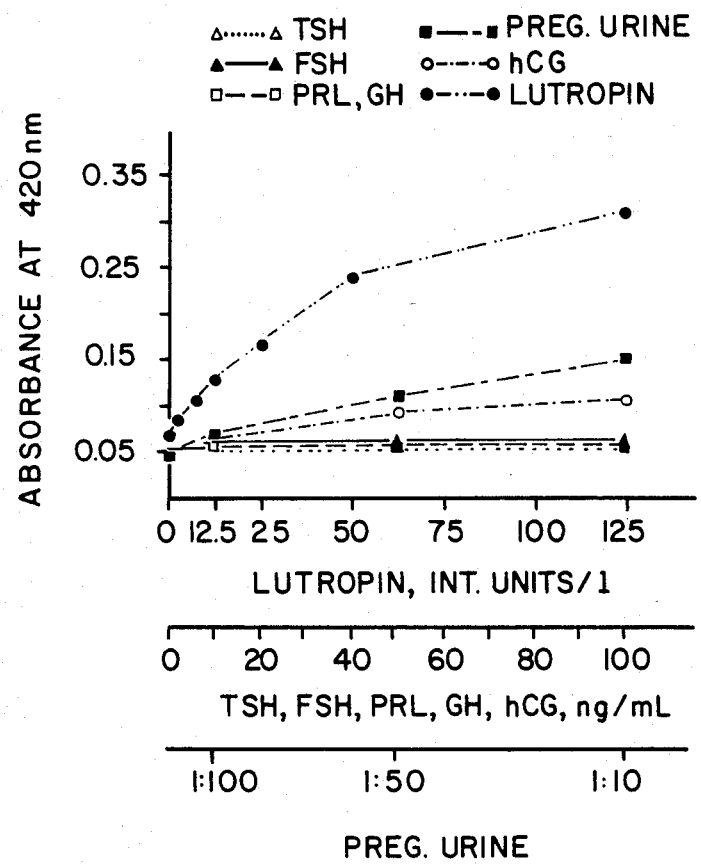
FIG. 11: Cross-reactivity of TSH, FSH, PRL, GH, HCG, and urine from a pregnant woman, in an enzyme-immunoassay of LH. Beads/tubes were used with simultaneous incubation.

The specificity of the enzyme-immunoassay was determined by testing the cross-reactivity with FSH, TSH, GH, hCG, PRL and pregnancy urine. As FIG. 11 demonstrates, there was no cross-reactivity at 10-fold concentrations of TSH, FSH, PRL and GH in the enzyme-immunoassay of LH. hCG in urine from a pregnant woman showed slight cross-reactivity in the enzyme-immunoassay of LH at a 2-fold concentration.

The validity of the enzyme-immunoassay of the present invention was checked by simultaneous assay of urine samples collected every day from day 9 to day 15 of the menstrual cycle in both enzyme-immunoassay and in a radio-immunoassay of LH. The results are shown in FIGS. 12 and 13.

Figure 12:
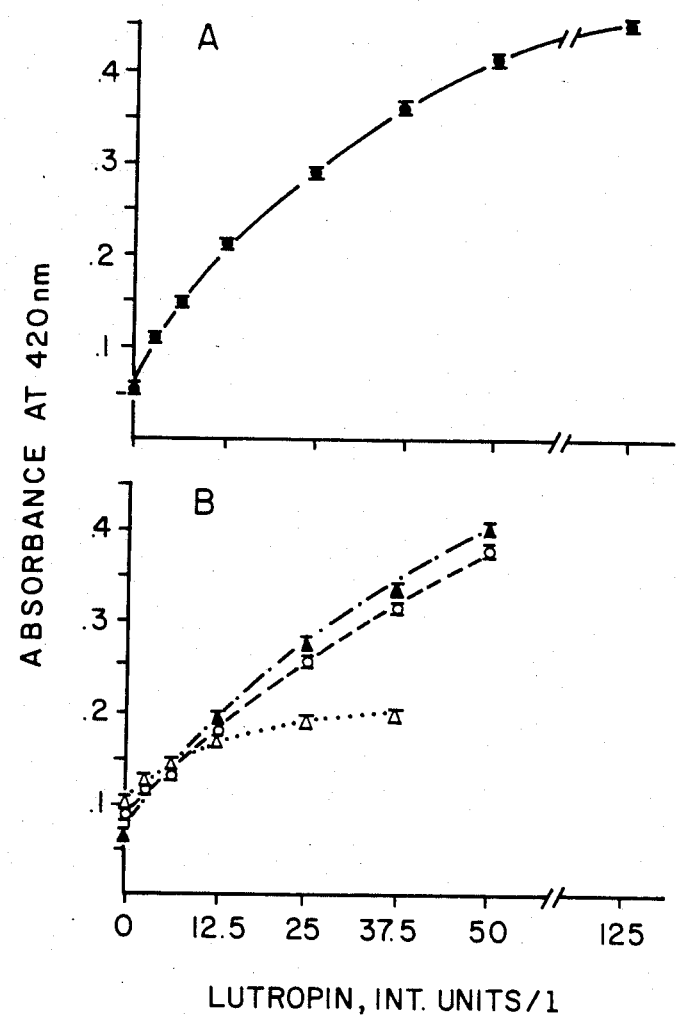
FIG. 12: Standard curves for LH in an enzyme-immunoassay using tubes/beads with simultaneous incubation. A: LH standards in radio-immunoassay buffer. B: LH standards in urine undiluted (Δ—Δ); 1:2.5 dilution: (○—○); and 1:5 dilution (Δ—Δ).

The standard curves for the enzyme-immunoassay of LH in radio-immunoassay buffer and in urine are shown in FIG. 12 using a polystyrene beads as well as polystrene tubes as the solid phases. Since undiluted urine showed the presence of substances interfering with the enzyme-immunoassay (see FIG. 12B), the urine samples were diluted to minimize the interference. A 1:2.5 to 1:5 dilution was optimum and showed a linear response, maximum sensitivity and virtually no interference in the assay. Various batches of the urine samples showed similar slopes with little differences in the y-intercept. The reproducibility of the enzyme-immunoassay, when four identical samples were assayed, was 95% to 105%.

Figure 13:
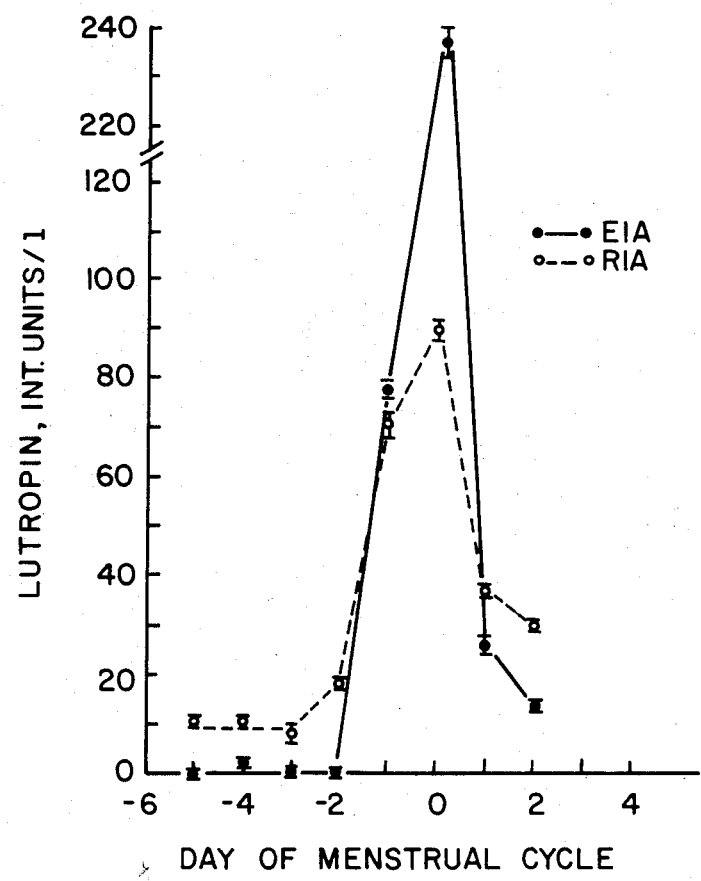
FIG. 13: Comparison of the enzyme-immunoassay and radio-immunoassay of LH.

As FIG. 13 demonstrates, the enzyme-immunoassay of the present invention correlates to results using a radio-immunoassay.

While the invention has been described in detail and with reference to specific embodiments thereof, it will be apparent to one skilled in the art that various changes and modifications can be made therein without departing from the spirit and scope thereof.

We claim:

1. A "sandwich" enzyme-immunossay for measuring hormone concentration in a sample, comprising the steps of:
    (1) immobilizing on a substrate, an antibody specific to a hormone to be assayed;
    (2) incubating the immobilized hormone specific antibody with the sample to be assayed;
    (3) adding a reagent comprising a purified polymer of a purified γ-globulin fraction of hormone-specific antibody: enzyme conjugate to the product of step (2), wherein said γ-globulin fraction is conjugated to said enzyme by means of a heterobifuntional cross-linking agent;
    (4) removing the unbound polymer of purified γ-globulin fraction of hormone-specific antibody: enzyme conjugate, from the product of step (3); and
    (5) assaying the enzyme in the resulting conjugate of step (4) and using the assay to measure concentration of the hormone in the sample.

2. The "sandwich" enzyme-immunoassay as in claim 1, wherein said hormone is lutropin.

3. The "sandwich" enzyme-immunoassay as in claim 1, wherein said enzyme is selected from the group consisting of alkaline phosphatase and horse radish peroxidase.

4. The "sandwich" enzyme-immunoassay as in claim 3, wherein said enzyme is alkaline phosphatase.

5. The "sandwich" enzyme-immunoassay as in claim 1, wherein said heterobifunctional cross-linking agent is m-maleimidobenzoyl N-hydroxy-succinimide ester.

6. The "sandwich" enzyme-immunoassay as in claim 1, wherein said substrate is selected from the group consisting of polystyrene tubes, polystyrene beads, glass beads, powder and sticks.

7. The "sandwich" enzyme-immunoassay as in claim 6, wherein said substrate is a polystyrene tube.

8. The "sandwich" enzyme-immunoassay as in claim 1, wherein said sample to be assayed is selected from the group consisting of blood, urine, scrum and spinal fluid.

9. The "sandwich" enzyme-immunoassay as in claim 1, wherein steps (2) and (3) are conducted simultaneously.

* * * * *